United States Patent [19]

Honeycutt

[11] Patent Number: 4,960,594

[45] Date of Patent: Oct. 2, 1990

[54] POLYURETHANE FOAM DRESSING

[75] Inventor: Travis W. Honeycutt, Irvine, Calif.

[73] Assignee: Derma-Lock Medical Corporation, Norcross, Ga.

[21] Appl. No.: 247,871

[22] Filed: Sep. 22, 1988

[51] Int. Cl.$^5$ .............................................. A61L 15/00
[52] U.S. Cl. ...................................................... 424/445
[58] Field of Search ......................................... 424/445

[56] References Cited

U.S. PATENT DOCUMENTS

| 3,709,221 | 1/1973 | Riely | 128/156 |
| 3,718,532 | 2/1973 | Hayes, Jr. | 161/159 |
| 3,778,266 | 12/1973 | Mizuno | 96/36.1 |
| 3,975,567 | 8/1976 | Lock | 428/315 |
| 3,978,855 | 9/1976 | McRae | 128/156 |
| 4,233,969 | 11/1980 | Lock et al. | 128/156 |
| 4,625,720 | 12/1986 | Lock | 128/156 |

OTHER PUBLICATIONS

Alvarez et al., Healing Wounds: Acclusion or Exposure, *Infections in Surgery*, (Mar., 1984).
Winter, Investigations of Polyurethane Foam Dressings on Shallow Wounds in the Domestic Pig, *Royal National Orthopaedic Hospital* (Dec., 1970).
Barnett et al., Scalp as Skin Graft Donor Site: Rapid Reuse with Synthetic Adhesive Moisture Vapor Permeable Dressings, *The Journal of Trauma*, vol. 23, No. 2 (1982).

*Primary Examiner*—Merrell C. Cashion, Jr.
*Assistant Examiner*—Leon R. Horne
*Attorney, Agent, or Firm*—Limbach, Limbach & Sutton

[57] ABSTRACT

A polyurethane foam wound dressing and a method for making the dressing is described. The dressing is made from the reaction of a polyurethane prepolymer with a difunctional cross-linking agent in the presence of DMEA and substantial amounts of water. The resulting dressing has a glazed, mirror-smooth surface for application to the wounded area and an insular region to maintain the wound at near body temperature. The dressing has a moisture vapor transmission rate that is close to the capacity of the wound surface to produce serous exudate.

16 Claims, No Drawings

POLYURETHANE FOAM DRESSING

TECHNICAL FIELD

The subject invention relates generally to protective dressings and more specifically to a polyurethane foam dressing for use over a wounded surface.

BACKGROUND OF THE INVENTION

Abrasions, burns, skin grafts and other similar wounds heal best when protected by a bandage or other dressing. Numerous protective devices have been used to facilitate the healing process. Absorbent, fibrous materials such as cotton gauze, quite common in the past, have proved unsatisfactory for many wounds. These bandages have a tendency to damage the wound surface by causing excessive dehydration of the wound. The cotton fibers tend to adhere to the wound surface, thus causing further damage to the wounded area when the dressing is removed or changed. Additionally, cotton fibers can become impregnated in the wound and impede the healing process.

It is taught by Alvarez, et al., Healing Wounds: Acclusion or Exposure, *Infections in Surgery*, (March 1984) that a moist wound environment inhibits scab development and allows epidermal cells to move freely over the moist dermal surface to enhance healing. Several synthetic bandages have thus developed in an attempt to circumvent the problems inherent in the older cotton dressings. For instance, Winter in Investigations of Polyurethane Foam Dressings on Shallow Wounds in the Domestic Pig, *Royal National Orthopaedic Hospital*, (Dec. 23, 1970), teaches that dressings made of polyethylene, polypropylene and polyamide films have been developed which are non-adherent and fully occlusive. Although occlusive conditions appear to promote epithelialization, excess liquid exudate produced by the wound cannot be absorbed by these dressings and liquid pools develop between the dressing and the wound. These pools are conducive to bacterial growth causing wound infection thus delaying the healing process. The accumulation of excess liquid can also cause delamination of the adhesive bandage causing the bandage to become loose and fall off.

Dressings made of polyurethane foam, although more absorbent, have a tendency to damage the wound surface by delaying re-epithelialization. These bandages are often fully open celled with a microfibril face, allowing for a very rapid water vapor transmission rate. Thus, the treated wound tends to dry out and the bandage becomes adherent and encapsulated by the serous scab that forms during healing. The low tensile strength of these polyurethane dressings further aggravates this problem by causing the bandage to tear at the dressing-/wound interface leaving the non-wetted foam embedded in the serious scab. The presence of the foreign polyurethane material in the epidermal and dermal layers can lead to foreign body reactions, excess fibrosis and hence scarring. As noted by Winters, these bandages leave impressed creases in the new tissue formed which can take up to two weeks to disappear.

As taught by Barnett, et al., Scalp as Skin Graft Donor Site: Rapid Reuse with Synthetic Adhesive Moisture Vapor Permeable Dressings, *The Journal of Trauma*. (Vol. 23, No. 2, 1982) other state of the art polyurethane bandages include synthetic, adhesive, moisture vapor permeable dressings which are non-foam, thin film, hydrophobic dressings. These bandages alleviate some of the prior art problems and encourage advanced healing rates, however, they exhibit adhesive properties which may interfere with healing and may retard the re-epithelialization upon removal and redressing. Further, these dressings lack insulation properties necessary to enhance the healing process.

U.S. Pat. No. 3,709,221 describes a composite surgical dressing made from high tensile fiberglass with a fluffy, fibrous absorbent layer. The bandage, however, tends to be stiff and rigid. U.S. Pat. No. 3,718,532 discloses a porous plastic made from an emulsion blended plastic substrate. Openings within the dressing are controlled by removal of the solvent during processing. The bandage is rendered lyophilic by the application of heat and pressure. U.S. Pat. Nos. 3,718,532, 3,975,567, 3,978,266 and 3,978,855 all describe dressings made from polymeric urethane also rendered lyophilic by the application of heat and pressure. This process produces a stiff and boardy bandage that is not easily pliable. Polyurethane dressings described in U.S. Pat. Nos. 4,233,969 and 4,625,720 require that polymerization take place in the near absence of water. The lack of water results in a bandage that is not sufficiently pliable to conform closely to the wound area and must be maintained by additional dressings or adhesive tape. Further, the absence of water during the reaction precludes $CO_2$ formation that causes foaming and more desireable moisture vapor transmission rates.

The present invention overcomes the above-noted shortcomings of conventional wound dressings. The subject dressing promotes healing by allowing the wound to remain moist but at the same time preventing the accumulation of liquid exudate. This is accomplished by providing a dressing with a carefully balanced moisture vapor pressure transmission rate that more accurately matches the capacity of the wound surface to produce serous exudate. Moreover, the dressing possesses an insular property which helps maintain the wound at body temperature, thus enhancing the healing process. Further, the surface of the bandage which faces the wound is non-adherent, mirror smooth and microporous so that damage to the wound will not occur upon removal of the dressing. These and other advantages of the subject invention will become apparent to those skilled in the art upon a reading of the Description of the Preferred Embodiment together with the drawings.

SUMMARY OF THE DISCLOSURE

A wound dressing material and a method for making the material is disclosed. The material is a non-adherent, thin film, foam polyurethane membrane cast on a substrate. The membrane is formed in the presence of a substantial amount of water and has a substantially smooth surface for application to the wound. An insular region is adjacent to the smooth surface for maintaining the wound near body temperature.

The membrane is formed from a polyurethane prepolymer with isocyanate residues, in the presence of a catalyst and a cross-linking agent with at least two groups capable of reacting with the isocyanate residues. The reaction product is cast onto an appropriate substrate and cured in the presence of a substantial amount of water. The resultant membrane has a moisture vapor transmission rate greater than 0.30 grams/inch$^2$/day.

DESCRIPTION OF THE PREFERRED EMBODIMENT

In accordance with the present invention, a wound dressing material is produced with improved properties. The bandage has the ability to absorb a limited amount of liquid exudate thus keeping the injured area moist while preventing liquid pools from forming which could serve as a medium for bacterial growth. The bandage will not adhere to or become impregnated in the wound. Further, the dressing is permeable to air which prevents the growth of anaerobic bacteria. Additionally, the dressing has an insular property to maintain the wounded area near body temperature and hasten epithelialization.

The improved dressing is made by the reaction of a polyurethane prepolymer with a cross-linking agent and a catalyst. Polymerization occurs in the presence of substantial amounts of water to enhance $CO_2$ formation.

Polyurethanes are formed from the reaction of approximately equimolar quantities of dihydroxy alcohols with diisocyanates in the following general reaction:

$$n(HOROH) + n(OCN-R_1-NCO) \longrightarrow$$
$$[-O-R-O-\underset{\underset{O}{\|}}{C}-\underset{}{N}\underset{H}{}-R_1-\underset{H}{N}-\underset{\underset{O}{\|}}{C}-]_n$$

When carried out in the presence of water, $CO_2$ is formed by the reaction of water with the isocyanate residues as follows:

$$RNCO + H_2O \rightarrow RNH_2 + CO_2$$

The $CO_2$ evolved causes the elastomeric polyurethane to swell and ultimately collapse during curing, as described below, with the formation of voids or cells. By varying the reaction conditions, polyurethane foams with differing cell characteristics can be formed. These voids are in part responsible for the improved characteristics demonstrated by the present invention.

Reactants found most useful with the present invention include polyurethane prepolymers which are midrange molecular weight polymers with residual isocyanate groups available for reaction. These prepolymers are especially desireable as they avoid the potential for exposure to toxic diisocyanates. For example, prepolymers such as Hypol 2002, Hypol 2003, and Hydrogel, all sold by W.R. Grace & Co. (New York), are particularly useful in the present invention. Hypol is a polyoxyethylene diol with an average molecular weight of 1500, containing a proportion of polyols with three or more hydroxy groups, the diol and polyols having been capped with diisocyanates to create a reaction oligomer. Hypol 2003 is the reaction product of toluene diisocyanate and a polyethylene glycol diol with excess isocyanate groups available for reaction. Hydrogel is characterized as being approximately 7,000 grams per mol having a 0.6 meq/gram reactivity. Hypol 2003, on the other hand, is characterized at 1500 grams per mol, having a 2.0 meq/gram reactivity.

Although less desireable, the subject invention can be practiced without the use of pre-manufactured prepolymers. For example, a polyester, polyol or polyether can be reacted with a diisocyanate monomer to form a polyurethane polymer suitable for use with the present invention. Specifically, a polyether polyol such as Pluronic L-64 polyoxypropylene glycol or polyethyleneglycol such as NYAX, available from Union Carbide, can be added to the reaction mixture along with a diisocyanate such as toluene diisocyanate with an Index of 109, available from Lankro Chemicals. Such a reaction is described in U.S. Pat. No. 4,625,720. This reaction could be "stopped short" to form an oligomer or can be carried to completion to form a polymer.

Also included in the reaction mixture of the present invention is a cross-linking agent to react with and cross-link the residual isocyanate groups present on the prepolymer used. The cross-linking agent is preferably difunctional with two or more groups reactive with isocyanate. Cross-linking agents with terminal hydroxyl, amine, carboxyl and carbonyl groups have found use with the present invention. Particularly useful is a silicone polyethylene oxide copolymer with terminal hydroxyl groups, such as Surfactant 193 from Dow Corning. Also useful is an ethylene glycol/propylene glycol copolymer sold under the trade name Pluronic L-64 and available from BASF. Several other alkylene oxide surfactants will also find use with the present invention, such as Pluronic 17R1 and 25R2 available from BASF, Tergitols and NYAX available from Union Carbide, various polyols available from Dow Chemical Co., and BRIJ available from ICI.

A catalyst should also be present in the mixture to drive the reaction. The catalyst can be organic or inorganic, so long as it does not interfere with the cross-linking agent present. Particularly useful are tertiary amines or other nucleophiles which cannot react through the amine function but can react through a hydroxyl group. For example, dimethylethanolamine (DMEA), available from Lankro Chemicals and sold under the trade name Propamine A, is particularly useful with the present invention. Other suitable catalysts include those enumerated in U.S. Pat. No. 4,233,969 to Lock, et al., dated Nov. 18, 1980, the disclosure of which is incorporated herein by reference. More specifically, further catalysts include polyols having three or more hydroxyl groups, the diol and polyols having been capped with di-isocyanates. The preferred cross-linking agent or catalyst is dimethylethanolamine. Other crosslinking agents or catalysts may be selected from the group comprising diethylenetriamine, triethylenetetramine, tetraethylenepentamine, polyethyleneimine, glycerol, trimethylolpropane, pentaerythritol, tolylene-2,4,6-triamine, ethylene diamine, amino-ethanol, trimethylenediamine, tetramethylenediamine, pentamethylenediamine, hexamethylenediamine, ethanolamine, diethanolamine, hydrazine, triethanolamine, benzene-1,2,4-tricarboxylic acid, nitrilotriacetic acid, citreic acid, 4, 4'-methylenebis (o-chloroaniline) and organic salts of tin and mercury. The alkylene surfactant may contain ethylene oxide and propylene oxide, and the proportions of these may lie in the range from 75:25% to 40:60% by weight.

After the reactants are combined, they are spread on a smooth substrate. Suitable substrates include any surface capable of leaving a mirror-smooth surface on the membrane when the substrate is removed. This is the surface of the membrane that will ultimately be in contact with the wounded area. Particularly suitable for use is a smooth, glazed release paper such as Mead release paper W89 SPT 3A/P. Other useful substrates include silicone or polyethylene treated films or papers. The polyurethane foam is then cured at approximately room temperature in relatively high humidity, ranging from 55 to 100%, preferably 60 to 75% and ideally 68% relative humidity. The foam is cured from 4 to 24 hours, preferably 8 hours, at temperatures up to 100° F, or until such time as the foam raises and collapses.

The resulting product possesses the following unique properties. First, it displays a low specific gravity yet does not easily tear expressing remarkable strength. Furthermore, the product is remarkably comfortable possessing excellent insulating properties. Additionally, the dressing is asymmetrical with respect to hydrophilicity and hydrophobicity. This property is thought to contribute to the greatly improved moisture vapor transmission rate that allows water or liquid exudate to be absorbed, but at the same time does not dehydrate the wounded area. Further, the dressing has an insular property to maintain the wound at body temperature. The bandage permits air to perfuse therethrough, has a non-adherent, mirror smooth surface for application to the wounded area and is highly flexible for contouring purposes.

Experimental

In order to demonstrate the invention, the following experiments were carried out with a variety of reactants. It should be understood that these examples are merely illustrative and are not intended to limit the scope of the claims.

All quantities labelled percent (%) are grams per 100 milliliters, unless otherwise indicated. All weights are given in grams (g) or milligrams (mg), and all volumes are given in liters (L), milliliters (ml) or cubic centimeters (cc) unless otherwise indicated.

Determination of Water Vapor Transmission Rate

The water vapor transmission rates (WVTR) in the experiments below were determined by placing 150 g. of water in a glass bottle. The glass bottle had an opening with a three inch inner diameter. The opening was covered with the material to be tested and the material wired in place. No tension was placed on the samples. This test was carried out at approximately 70±2° F. at 50% RH. The test was carried out for six days with the experimental apparatus being weight on days 1, 2, 3, and 6. The water vapor which was transmitted was that daily loss of weight, noting that the weight measurements were taken at approximately the same time each day.

Determination of Absorbance

Absorbance was determined by weighing the samples while dry and then immersing the samples in tap water at 25° C. for 24 hours. The samples were then removed from the water bath, extraneous droplets of water carefully removed by gentle shaking for one minute and the samples immediately weighed. The percent absorbance was calculated by comparing the dry weight with the wet weight.

EXAMPLE I

A polyurethane foam dressing was produced via the following method. 1550 g of Hypol 2003 (W.R. Grace, New York) was added to a stainless steel pan and whipped with an electric stirrer for 90 seconds to approximately double its volume. To the whipped mixture was added a mixture of 54 ml of Pluronic L-64 (BASF) and 12 cc of dimethyaminoethanol available from Eastman Kodak Co. as a drizzle over two minutes while stirring vigorously. The mixture was scraped onto Mead release paper W89 SPT 3A/P and sent through a kiss roll coater to a thickness of 0.020 inches. The mixture was placed immediately to cure and held at 68° F./ at 68% relative humidity. Within thirty minutes, the film was rising from the evolution of $CO_2$ and within 60 minutes was at a height of 0.250 to 0.400 inches. The film ultimately reached a height of 0.500 inches. The cell structure was established before the complete evolution of $CO_2$, as the film started to shrink after two hours. The film was cured for a period of eight hours and had a final film height of 0.080 to 0.090 inches.

It is thought that air entrainment forms the cells and that $CO_2$ diffuses into the formed cells to expand or stretch them during cure. This in turn results in the unique and surprising properties demonstrated by the film. This product was satisfactory as a wound management device. The properties of the dressing thus produced are given in Table 1.

EXAMPLE II

The procedure from Example 1 was repeated with the exception that the reaction mixture was cured in the near absence of water at approximately 130° F. and an RH of 20%. The resulting film was much thinner, stiffer and nearly non-conformable when applied to a continuous curved structure such as a face, knee or elbow. The dressing had a glossy surface but had a noticeable lack of cellular structure throughout the membrane. The properties of the membrane thus produced are given in Table 1.

EXAMPLE III

The procedure was carried out as in Example I with the exception that 1.5 cc of FC 430 (3M) a fluorinated hydrophobic material, was added as a cast film coater to synthetically reproduce the anhydrous conditions of Example II. The cast film did not rise and separated into puddles due to the lack of moisture. After eight hours, the film was still not cured and had holes of ½ inch diameter or greater. The properties of the membrane thus produced are given in Table 1.

EXAMPLE IV

The procedure from Example I was repeated with the exception that Hydrogel (W.R. Grace, New York) was substituted for the Hypol 2003. The sample was cured for eight hours at 68° F. and 68% relative humidity. The membrane produced had surprisingly outstanding compliance, excellent cellular formation, low density, low relative absorbance and a desireable WVTR. The properties of the membrane thus produced are given in Table 1.

EXAMPLE V

The procedure from Example IV was repeated with the exception that Surfactant 193 (Dow Corning) was substituted for the Pluronic L-64. The product exhibited surprisingly exceptional characteristics, including superior conformance, WVTR and absorbance. The properties of the membrane thus produced are given in Table 1.

TABLE 1

| SAMPLE | SIZE | SQUARE AREA | THICKNESS | WEIGHT | DENSITY | WVTR (g/in$^2$/day) | WATER ABSORBANCE |
|---|---|---|---|---|---|---|---|
| Ex. 1 | "4 × 4" | 16" (103.23 cm) | 0.070" (0.177 cm) | 3.2 g | 3.2 g/ 18.354 cm$^3$ (0.1743) | 0.49 | 131% |
| Ex. 2 | "4 × 4" | 16" (103.23 cm) | 0.075" (0.1905 cm) | 3.4 g | 3.4 g/ 19.665 cm$^3$ (0.1729) | 0.43 | — |
| Ex 3 | "4 × 4" | 16" (103.23 cm) | 0.022" (0.056 cm) | 3.4 g | 3.4 g/ 5.781 cm$^3$ (0.588) | No continuous film to evaluate | |
| Ex 4 | "4 × 4" | 16" (103.23 cm) | 0.075" (0.1905 cm) | 3.4 g | 3.4 g/ 19.665 cm$^3$ (0.1729) | 0.59 | 112% |
| Ex. 5 | "4 × 4" | 16" (103.23 cm) | 0.070" (0.1778 cm) | 2.8 g | 2.8 g/ 18.354 cm$^3$ (0.1526) | 0.38 | 21% |
| Opsite | "3.88" × "5.50" | 21.34" (137.7 cm) | 0.0015e (0.004 cm) | 0.7 g | 0.79/0.55 cm$^3$ (1.27) | 0.15 | 57% |
| Tegaderm | "3.88" × "5.50" | 21.34" (137.7 cm) | 0.003e (0.008 cm) | 1.4 g | 1.48/1.1 cm$^3$ (1.27) | 0.14 | 37% |

EXAMPLE VI

The following samples were weighed and immersed in tap water at 25° C. and held for 24 hours to test water absorption. The samples were then removed from the water bath, extraneous droplets of water carefully removed by gently shaking for one minute and the samples immediately weighed. The percent absorbance was calculated by comparing the dry weight with the wet weight. The results of the experiment are given in Table 2.

TABLE 2

| | Size (In.$^2$) | Dry Wt. | Wet Wt. | G. Moisture Absorbed | % Absorption |
|---|---|---|---|---|---|
| Opsite | 21.3 | 0.7 g | 1.1 g | 0.4 | 57 |
| Tegaderm | 21.3 | 1.4 g | 1.9 g | 0.5 | 36 |
| Example I | 16.0 | 3.2 g | 7.4 g | 4.2 | 131 |
| Example IV | 16.0 | 3.4 g | 7.2 g | 3.8 | 112 |
| Example V | 16.0 | 2.8 g | 3.4 g | 0.6 | 21 |

Opsite and Tegaderm are polyurethane non-foam film dressings sold by Smith and Nephew and 3M, respectively. As can be seen, the dressings produced by Examples 1 and 4, according to the present invention, exhibited far greater absorbance than the polyurethane non-foam films tested. It is believed that the bulk of moisture absorbed by the non-foam films was due to the adhesive present on these films and not as a result of the polyurethane non-foam film themselves.

EXAMPLE VII

The water vapor transmission rates of the products of Examples I, II, IV and Opsite and Tegaderm (described above) were compared by the method described previously. The results of this experiment can be seen in Table 3.

TABLE 3

RATE OF WATER TRANSMISSION (CCH$_2$O/Inch/Day)

| SAMPLE | 1st | 2nd | 3rd | 4-6 days | AVG. |
|---|---|---|---|---|---|
| Ex I | 0.48 | 0.51 | 0.48 | 1.45 | 0.49 |
| Ex II | 0.33 | 0.51 | 0.41 | 1.35 | 0.43 |
| Ex IV | 0.50 | 0.66 | 0.75 | 1.63 | 0.59 |
| Ex V | 0.40 | 0.45 | 0.35 | 0.35 | 0.38 |
| OPSITE | 0.01 | 0.25 | 0.11 | 0.51 | 0.15 |
| TEGADERM | 0.01 | 0.26 | 0.08 | 0.48 | 0.14 |

As can be seen in Table 3, the dressings produced by Examples I and IV, according to the present invention, exhibited greater water vapor transmission rates than that produced by the method lacking substantial moisture and by the polyurethane non-foam films tested. The higher water vapor transmission rates are thought to more accurately match the production of liquid exudate from the wounded area. Thus, pooling of exudate is prevented, but at the same time the wound area is kept sufficiently moist to prevent adherence of the dressing to the wound and hasten the healing process.

Thus, an improved polyurethane foam dressing has been described. Although a preferred embodiment of the system has been described in some detail, it is understood that obvious variations can be made without departing from the spirit and the scope of the invention as defined by the appended claims.

What is claimed is:

1. A wound dressing material consisting essentially of a nonadherent, thin film, foam polyurethane membrane having a substantially smooth surface for application to a wounded area and an insulating region adjacent said smooth surface for maintaining the wound near body temperature, wherein said wound dressing is formed in the presence of a substantial amount of water to enhance CO$_2$ formation and exhibits a moisture vapor transmission rate greater than 0.30 grams/inch$^2$/ day.

2. The wound dressing of claim 1 wherein said membrane has a density less than 0.6 grams/centimeter$^3$.

3. The wound dressing of claim 1 wherein said membrane exhibits an absorbance based on dry weight of greater than 20%.

4. The wound dressing of claim 1 wherein said membrane is formed by the reaction of a polyurethane prepolymer, a catalyst and a cross-linking agent.

5. The wound dressing of claim 4 wherein said polyurethane prepolymer is selected from the group consisting of a polyethyelene glycol diol with available isocyanate groups, a polyoxyethylene diol with available isocyanate groups, a mixture of a polyester and a diisocyanate, and a mixture of a polyether, a diisocyanate, and a polyoxypropylene diol capped with at least two diisocyanate end groups.

6. The wound dressing of claim 5 wherein said catalyst is selected from the group consisting of dimethyaminoethanol, diethylenetriamine, triethylenetetramine, tetraethylenepentamine, polyethyleneimine, glycerol, trimethylolpropane, pentaerythritol, tolylene-2,4,6-triamine, ethylene diamine, amino-ethanol, trimethylenediamine, tetramethylenediamine, pentamethylenediamine, hexamethylenediamine, ethanolamine, diethanolamine, hydrazine, triethanolamine, benzene-1,2,4-tricarboxylic acid, nitrilotriacetic acid, citric acid, 4,4'-methylenebis (o-chloroaniline), and organic salts of tin and mercury.

7. The wound dressing of claim 6 wherein said crosslinking agent is difunctional or greater with two or more terminal groups reactive with isocyanate residues present on said polyurethane prepolymer.

8. The wound dressing of claim 7 wherein said crosslinking agent is selected from the group consisting of an ethylene glycol/propylene glycol copolymer, silicone polyethylene oxide copolymer, polyethelyeneamines.

9. A wound dressing material consisting essentially of a nonadherent, thin film, foam polyurethane membrane formed by the reaction of a polyurethane prepolymer with isocyanate residues, a catalyst, and a cross-linking agent with two or more terminal groups reactive with the isocyanate residues, wherein said membrane is formed in the presence of substantial amounts of water to enhance $CO_2$ formation, and further wherein said membrane exhibits a moisture vapor transmission rate greater than 0.30 grams/inch$^2$/ day, said membrane further comprising a substantially smooth surface for application to a wounded area and an insulating region adjacent said smooth surface for maintaining the wound near body temperature.

10. A method for producing a non-adherent, thin film wound dressing material having a substantially smooth surface for application to the wounded area and an insular region adjacent said smooth surface, said method comprising the steps of:

reacting a polyurethane prepolymer having isocyanate residues, a catalyst, and a crosslinking agent with two or more terminal groups capable of reacting with the isocyanate residues, to form a mixture;

placing the mixture on a substrate;

curing the mixture on the substrate in the presence of a substantial amount of water to enhance $CO_2$ formation to form a membrane with a moisture vapor transmission rate greater than 0.30 grams/inch$^2$/day.

11. The method of claim 10 wherein the mixture is cured at approximately room temperature and at a relative humidity of between 60 to 80%.

12. The method of claim 10 wherein said membrane has a density less than 0.6 grams/centimeter$^3$.

13. The method of claim 10 wherein said membrane exhibits an absorbance based on dry weight of greater than 60%.

14. The wound dressing of claim 4 wherein said polyurethane prepolymer is selected from the group consisting of a polyethyelene glycol diol with available isocyanate groups, a polyoxyethylene diol with available isocyanate groups, a mixture of a polyester and a di-isocyanate, and a mixture of a polyether and a di-isocyanate.

15. The method of claim 10 wherein said catalyst is selected from the group consisting of dimethyaminoethanol, diethylenetriamine, triethylenetetramine, tetraethylenepentamine, polyethyleneimine, glycerol, trimethylolpropane, pentaerythritol, tolylene-2,4,6-triamine, ethylene diamine, amino-ethanol, trimethylenediamine, tetramethylenediamine, pentamethylenediamine, hexamethylenediamine, ethanolamine, diethanolamine, hydrazine, triethanolamine, benzene-1,2,4-tricarboxylic acid, nitrilotriacetic acid, citric acid, 4,4'-methylenebis (o-chloroaniline), and organic salts of tin and mercury.

16. The method of claim 10 wherein said cross-linking agent is selected from the group consisting of an ethylene glycol/propylene glycol copolymer, silicone polyethylene oxide copolymer, polyethyleneamines.

* * * * *